(12) United States Patent
Koest

(10) Patent No.: US 7,040,765 B2
(45) Date of Patent: May 9, 2006

(54) DEVICE FOR PROJECTING A LIGHT BEAM

(75) Inventor: Gert Koest, Hannover (DE)

(73) Assignee: Oculus Optikgeraete GmbH, Wetzlar-Dutenhofen (DE)

( * ) Notice: Subject to any disclaimer, the term of this patent is extended or adjusted under 35 U.S.C. 154(b) by 0 days.

(21) Appl. No.: 10/826,650

(22) Filed: Apr. 16, 2004

(65) Prior Publication Data

US 2004/0212786 A1    Oct. 28, 2004

(30) Foreign Application Priority Data

Apr. 25, 2003  (DE) .......................... 203 06 542 U

(51) Int. Cl.
*G03B 21/14*   (2006.01)
*A61B 3/135*   (2006.01)

(52) U.S. Cl. .................... 353/84; 359/211; 351/214

(58) Field of Classification Search .................. 353/46, 353/81; 359/211; 351/211, 214; 362/227, 362/800
See application file for complete search history.

(56) References Cited

U.S. PATENT DOCUMENTS

| 2,222,937 A | 11/1940 | Dimmick |
| 4,125,320 A | 11/1978 | Rassow et al. |
| 4,168,126 A | 9/1979 | Altman et al. |
| 4,272,165 A * | 6/1981 | Muchel et al. .............. 351/211 |
| 5,189,545 A | 2/1993 | Takata et al. |
| 5,742,426 A | 4/1998 | York |
| 5,815,242 A | 9/1998 | Anderson et al. |
| 6,698,894 B1 * | 3/2004 | Anderson ..................... 353/31 |
| 6,739,723 B1 * | 5/2004 | Haven et al. ................. 353/20 |
| 6,827,450 B1 * | 12/2004 | McGettigan et al. .......... 353/31 |
| 2004/0201827 A1 * | 10/2004 | Kojima ........................ 353/81 |
| 2004/0240020 A1 * | 12/2004 | Schanz ........................ 359/211 |
| 2005/0169572 A1 * | 8/2005 | Itoh ............................ 385/15 |

FOREIGN PATENT DOCUMENTS

| DE | 3543648 A1 | 6/1987 |
| DE | 4015920 A1 | 11/1990 |

* cited by examiner

*Primary Examiner*—William C. Dowling
(74) *Attorney, Agent, or Firm*—Flynn, Thiel, Boutell & Tanis, P.C.

(57) ABSTRACT

A device for projecting a light beam on an object includes a light source for generating the light beam and projection optics for transmitting the light beam from the light source to the object. At least one prism with at least two essentially plane-parallel surfaces is arranged in the beam path of the light beam between the light source and the object as part of the projection optics. The prism is movably supported and can be driven by a drive unit in such a way that the light beam is shifted in a parallel fashion by an amount (X) that depends on the position of the prism when the light beam passes through the plane-parallel surfaces of the prism.

19 Claims, 3 Drawing Sheets

DEVICE FOR PROJECTING A LIGHT BEAM

FIELD OF THE INVENTION

The invention pertains to a device for projecting a light beam on an object with a light source and projection optics.

Projection devices of this type are used, for example, in medical engineering for examining the human eye. However, the utilization of these projection devices is by no means limited to this field. Such projection devices are required, in particular, in ophthalmologic Scheimpflug cameras in order to project a light beam on the eye to be examined. In devices of this type, the light beam is generated by a light source, in which a directional light beam can be generated, for example, by converting electric energy. The projection optics, in principle, may be realized arbitrarily. In this respect, it would also be conceivable to realize devices, in which the projection optics do not contain any deflecting devices and lenses.

In numerous applications of such devices, it is desirable to distribute the illuminance as homogenously as possible in the light beam. Inhomogeneities in the illuminances may undesirably falsify the measuring results. One disadvantage of known devices is that most available light sources, for example, light bulbs with an electric filament or light sources composed of several light-emitting diodes, have a relatively inhomogenous distribution of the illuminance in the light beam. For example, if the light source consists of several light-emitting diodes, the emitted light of which is collectively focused and thusly forms the light beam, each individual light-emitting diode causes an illuminance maximum in the light beam.

Based on this state of the art, the present invention aims to propose a device for homogenizing the illuminance in the light beam generated by the light source with simple means.

SUMMARY OF THE INVENTION

The invention is based on the basic principle of shifting the light beam in a parallel fashion while it passes through a prism. For this purpose, the prism has at least two essentially plane-parallel surfaces. The light beam incident on the first surface of the prism is deflected by a certain angle, wherein the amount of this deflection depends on the relative position between the light beam and the surface of the prism. When the light beam emerges from the prism on the second surface, it is once again deflected by a certain angle. Due to the plane-parallel arrangement of the two prism surfaces, the deflection of the light beam on the two prism surfaces is exactly opposite and equal. This means that the light beam is shifted in a parallel fashion between the point at which it is incident on one prism surface and the point at which it emerges from the other prism surface.

Since the prism is supported in a movable fashion and driven by means of a drive unit, the light beam is constantly shifted within a certain range because the relative position between the prism and the light beam constantly varies. The shifting of the light beam takes place with a speed that depends on the moving speed of the prism.

According to the invention, the transmission of the light beam through a moving prism with at least two plane-parallel surfaces causes the illuminance maxima in the light beam to shift back and forward constantly such that they are uniformly distributed in the light beam. For example, when taking photographs of an object illuminated with such a light beam and the exposure time lies in a time range, in which the illuminance maxima already have shifted back and forward several times, it is no longer possible to distinguish the illuminance maxima in the photograph. The photographer consequently obtains a photograph with absolutely homogenous lighting conditions.

In the device according to the invention, it suffices, in principle, to utilize a prism with exactly two essentially plane-parallel surfaces. In order to simplify the kinematics in driving the prism, it is particularly advantageous if the prism contains several pairs of surfaces that respectively are arranged essentially plane-parallel to one another. It would be possible, in particular, to utilize prisms, the surfaces of which are uniformly distributed over the circumference of the prism and form a regular polygon with n corners. This would make it possible to drive the prism in a rotative fashion in order to achieve a simple homogenization of the illuminance in the light beam. It is not necessary to reverse the rotating direction in this case.

A particularly simple design of the prism can be achieved if the prism comprises four surfaces for the refraction of light beams, wherein two respective surfaces are arranged plane-parallel to one another.

In order to achieve a sufficient homogenization of the illuminance in the light beam when the light beam is incident on the object, the prism speed should not fall short of a certain minimum speed. For example, if the prism comprises four light refraction surfaces, it is particularly advantageous to drive the prism with a speed of no less than approximately 100 revolutions per second. At an exposure speed of 50 frames per second, the prism carries out two revolutions during the exposure of one frame. This means that the four prism surfaces cause the light beam to shift eight times between the maxima in a parallel fashion during the exposure of one frame. Illuminance maxima can no longer be detected in the individual frames in such instances.

A driving motor, particularly an electric motor, is provided for driving the prism. If so required, gears with a certain gear ratio may also be arranged between the prism and the driving motor.

According to one preferred embodiment of the invention, several prisms that are supported in a movable fashion and can be driven are arranged successively in the beam path. The homogenization of the illuminance can be improved with this measure if the prisms cause a parallel shift of the light beam in one plane.

According to another embodiment, the successively arranged prisms are respectively supported such that they can be turned about an axis of rotation, wherein the axes of rotation of the different prisms essentially extend perpendicular to one another. This causes a parallel shift of the light beam in a first plane on the first prism and a parallel shift in a plane that extends perpendicular to the first plane on the second prism. When utilizing a light source that emits an approximately punctiform light beam, for example, a laser light source, the laser light beam can be projected on a rectangular field in this fashion.

The device according to the invention is particularly advantageous in connection with light sources that emit an approximately line-shaped light beam. The term line-shaped light beam refers to a light beam, the propagation of which is approximately linear transverse to the beam direction. Such line-shaped light sources frequently have an inhomogenous illuminance due to, for example, the filament used or the arrangement of several light-emitting diodes adjacent to one another. These inhomogeneities can be reduced or entirely eliminated by means of the refraction in the moving prism.

If a series of lamps are arranged adjacent to one another and used as the light source, for example, light-emitting diodes, it is particularly advantageous if the light beam can be shifted in the prism by an amount that is greater than the distance between the respectively adjacent lamps. This causes the illuminance maxima to be shifted to such a degree during the movement of the prism that the shifting ranges overlap one another.

The device according to the invention is suitable, in principle, for all types of applications. The utilization of the device according to the invention is particularly advantageous in connection with slit projectors as they are used, for example, in Scheimpflug cameras. However, the device according to the invention is also well suited for use in other devices that serve for carrying out examinations on the human eye, namely because a largely homogenous illumination is usually desirable in these devices.

BRIEF DESCRIPTION OF THE DRAWINGS

Different embodiments of the invention are schematically illustrated in the figures and described in greater detail below.

The figures show.

DETAILED DESCRIPTION

Figure 1:
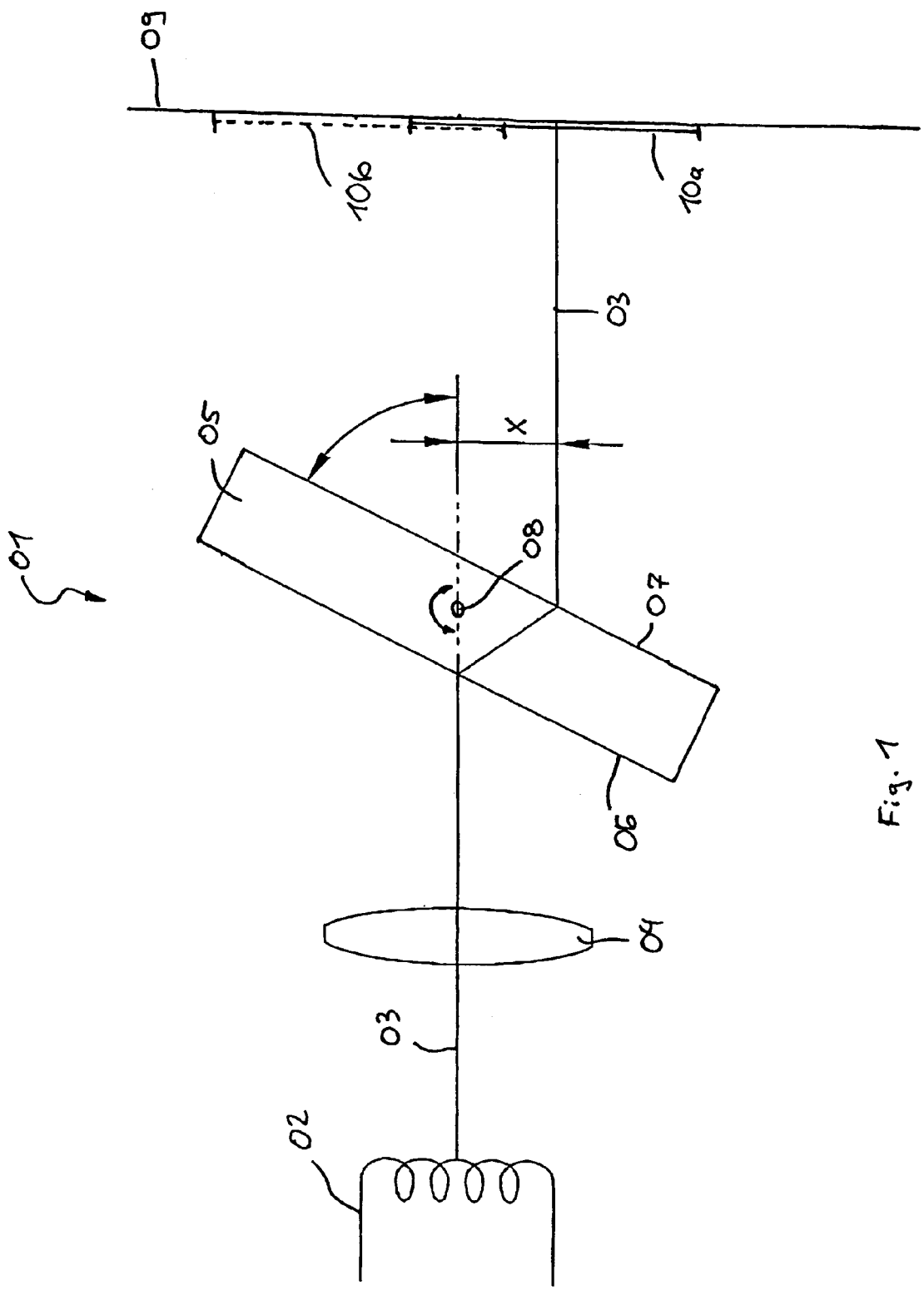
FIG. 1, the basic design of a first embodiment in the form of a top view.

FIG. 1 shows a schematic representation of a first embodiment 01 of the device according to the invention. A light source 02 in the form of a filament generates an essentially line-shaped light beam, the propagation of which approximately corresponds to the length of the filament 02. In order to better comprehend the invention, the light beam generated by the light source 02 in FIG. 1 is merely indicated in the form of the central beam axis that represents the light beam 03. A purely schematic illustration of the light beams was also chosen in other respects in FIG. 1-FIG. 3.

After the light beam 03 passes through a lens 04, it is incident on a prism 05 with two surfaces 06 and 07 that are arranged plane-parallel to one another. Due to the different optical density, the light beam 03 is refracted on these surfaces. The plane-parallel arrangement of the two surfaces 06 and 07 causes the light beam 03 to be laterally shifted in a parallel fashion by an amount X. The amount of the lateral shift of the light beam 03 depends on the angle α that represents the relative angle between the prism 05 and the beam axis of the light beam 03.

The prism 05 is supported such that it can be turned about an axis of rotation 08, wherein a not-shown drive is able to turn the prism alternately in the clockwise direction and the counterclockwise direction. Consequently, the prism 05 oscillates about a center position, in which the light beam 03 passes through the prism 05 without being deflected. The angle a shown in FIG. 1 represents the maximum position of the prism 05 in the clockwise direction.

After passing through the prism 05, the light beam 03 is incident on a projection surface 09 and projects the light source 02 thereon in the form of a streak of light 10. The streak of light 10a illustrated with a continuous line corresponds to the projection of the light source 02 when the prism 05 is situated in the maximum position according to FIG. 1, namely at the angle α. The length of the streak of light 10a corresponds to the length of the light source 02 after the projection through the converging lens 04. Another streak of light 10b is illustrated with broken lines in FIG. 1. The streak of light 10b corresponds to the projection of the light source 02 when the prism 05 is situated in the maximum position in the counterclockwise direction (not shown in FIG. 1). One can ascertain that the streak of light 10b is shifted upward on the projection surface 09 in comparison with the streak of light 10a. If the prism 05 is constantly moved up and down between the two end positions during the operation of the device 01, the streak of light 10 projected on the projection surface 09 oscillates between the extreme positions 10a and 10b. Inhomogeneities in the illuminance distribution in the light beam 03 are homogenized in this fashion in the overlapping regions between the streaks of light 10a and 10b.

Figure 2:
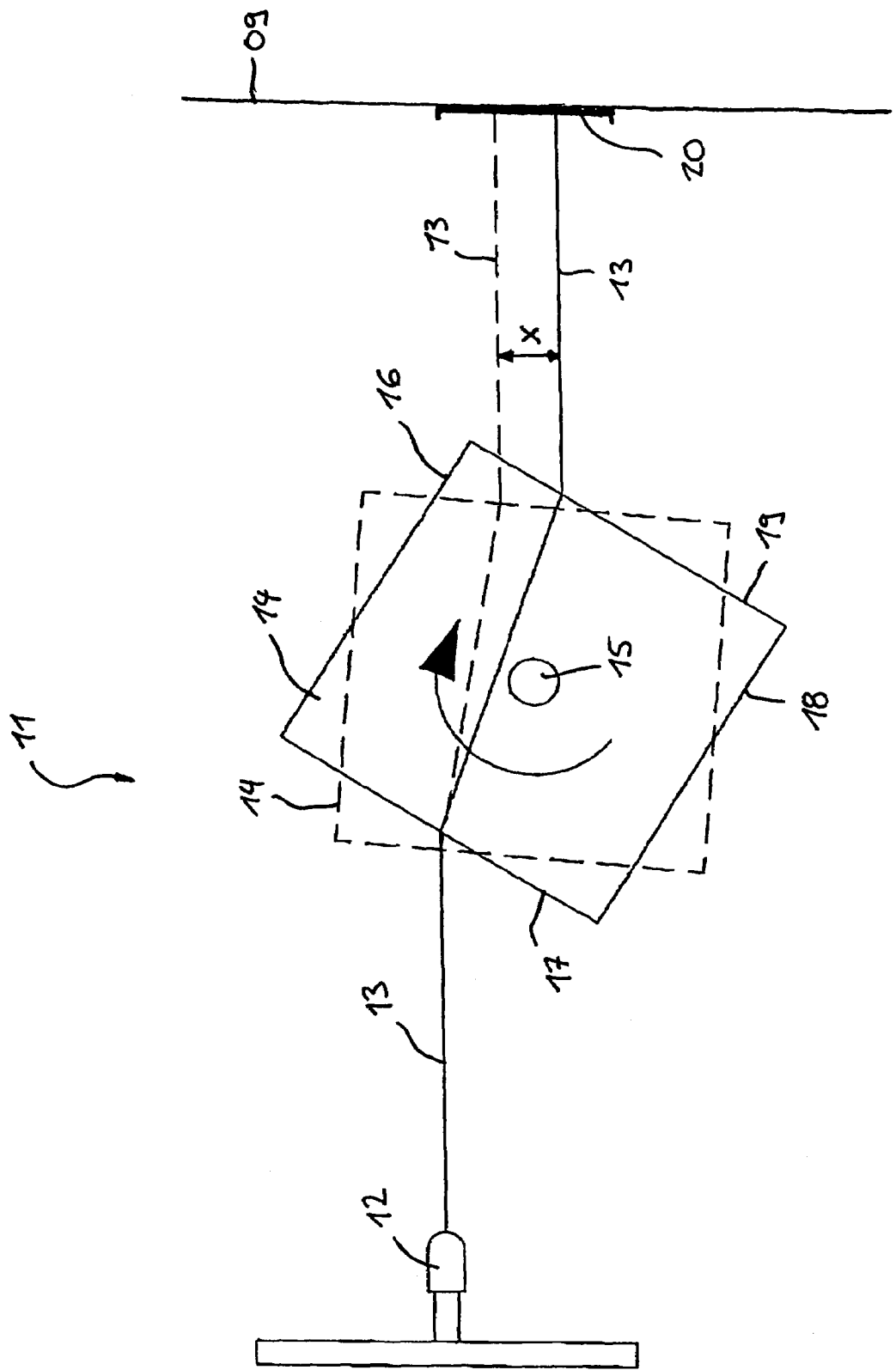
FIG. 2, the basic design of a second embodiment in the form of a top view.

FIG. 2 schematically shows a second embodiment 10 of the device according to the invention.

A light beam 13 that is focused in a punctiform fashion is emitted by a light source in the form of a laser diode 12 in this case. A prism 14 is arranged in the beam path of the light beam 13 and supported such that it can be turned about an axis of rotation 15, wherein the prism is rotatively driven in the clockwise direction by a not-shown driving motor. The prism 14 has four surfaces 16, 17, 18 and 19, on which the light beam 13 is refracted during its passage through the prism 14.

Depending on the angle of rotation of the prism 14, the light beam 13 is laterally shifted in a parallel fashion. The prism 14 according to FIG. 2 is illustrated in two positions with continuous lines and broken lines in order to better comprehend the invention. The corresponding beam paths of the light beam 13 are also illustrated with a continuous line and a broken line, respectively. If the prism is driven with a high speed, for example, 100 revolutions per minute, the light beam 13 is projected on the projection surface 09 in the form of a line-shaped streak of light 20. The length of the streak of light 20 depends on the maximum deflection of the light beam by the prism 14. Consequently, the highly focused light of the laser diode 12 can be projected in the form of a streak of light with essentially line-ship propagation by driving the movable prism 14, wherein the illuminance of the light is distributed accordingly.

Figure 3:
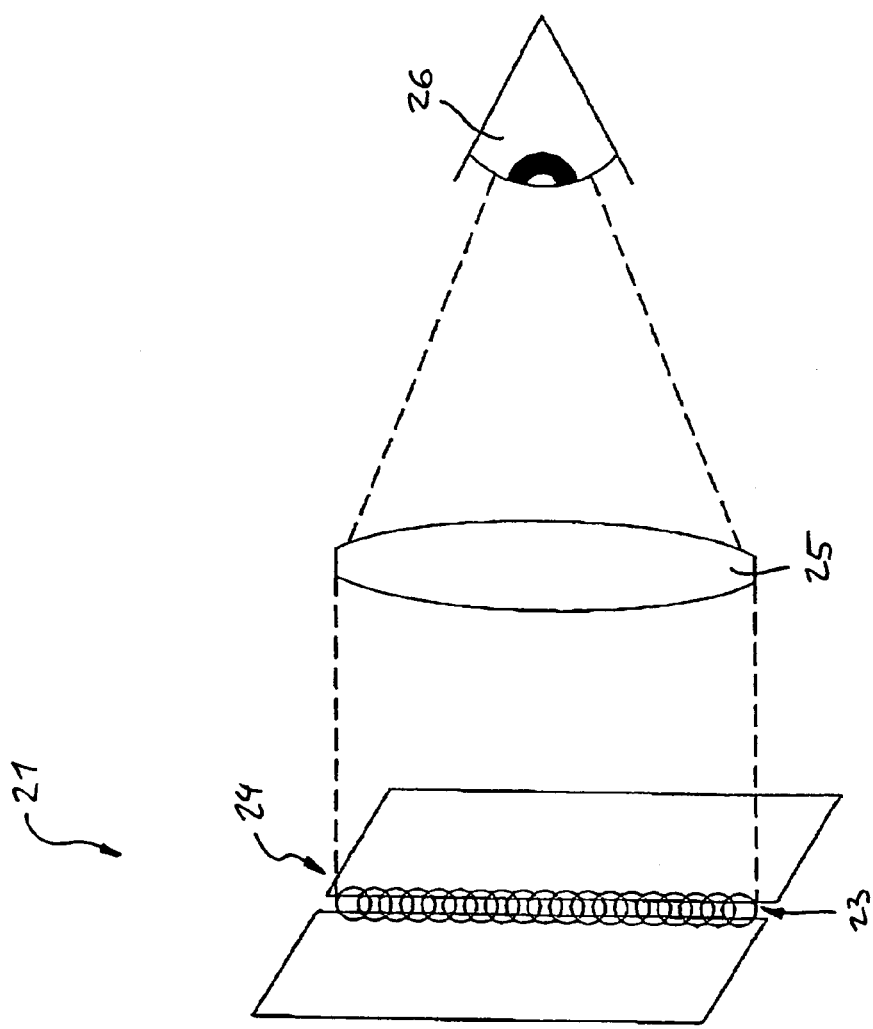
FIG. 3, the basic design of a third embodiment in the form of a top view.
Figure 3:
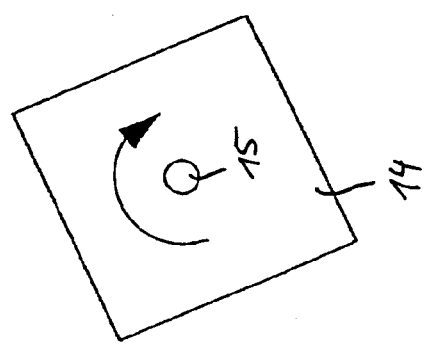
Figure 3:
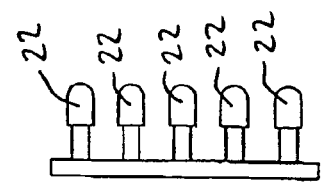

FIG. 3 shows a third embodiment 21 of the device according to the invention that is realized in the form of a slit projector as it may be used, for example, in a Scheimpflug camera for examining the human eye. The light source of the device 01 consists of five light-emitting diodes 22 that are adjacently arranged in a row and spaced apart from one another. These light-emitting diodes emit a line-shaped light beam, the propagation of which extends transverse to the beam axis in the direction of the slit 23 in the slit diaphragm 24.

The prism 14 is arranged in the beam path of the light beams emitted by the light-emitting diodes 22 and driven in the clockwise direction with a speed of at least 100 revolutions per minute. The prism 14 laterally shifts the light emitted by the respective light-emitting diodes 22 in a parallel fashion such that the light-emitting diodes 22 are projected several times in the slit 23 of the slit diaphragm 24 as schematically indicated in FIG. 3. The illuminance maxima of the different light-emitting diodes 22 overlap one another such that the illuminance distribution of the light beam is homogenized in the slit 23. This light beam with homogenized illuminance distribution is then projected on an eye 26 to be examined through a lens 25 in order to take photographs with a Scheimpflug camera that is not illustrated in FIG. 3.

The invention claimed is:

1. A device for projecting a light beam on an object, with a light source for generating the light beam, and with projection optics for transmitting the light beam from the light source to the object, wherein at least one prism with at least two essentially plane-parallel surfaces is arranged in a beam path of the light beam between the light source and the object as part of the projection optics, wherein the prism is movably supported to be at least one of turned and oscillated about an axis of rotation in a clockwise direction or in a counterclockwise direction and can be driven by a drive unit at a speed of at least approximately 100 revolutions per second, and wherein the light beam is shiftable in a parallel fashion by an amount that depends on the position of the prism when the light beam passes through the plane-parallel surfaces of the prism.

2. The device according to claim 1, wherein the drive unit comprises an electric driving motor.

3. The device according to claim 1, wherein the light source emits the light beam as an approximately punctiform light beam.

4. The device according to claim 1, wherein the light source comprises a lamp with an electrically heated filament.

5. The device according to claim 1, wherein the device forms part of an apparatus for carrying out examinations on the human eye.

6. The device according to claim 1, wherein the device forms part of an ophthalmologic Scheimpflug camera.

7. A device for projecting a light beam on an object, with a light source for generating the light beam, and with projection optics for transmitting the light beam from the light source to the object, wherein at least one prism with at least two essentially plane-parallel surfaces is arranged in a beam path of the light beam between the light source and the object as part of the projection optics, wherein the prism is movably supported and can be driven by a drive unit so that the light beam is shifted in a parallel fashion by an amount that depends on the position of the prism when the light beam passes through the plane-parallel surfaces of the prism, and wherein the device comprises additional movably supported prisms that can be driven and are successively arranged in the beam path.

8. The device according to claim 7, wherein the successively arranged prisms are each respectively supported for turning about an axis of rotation, wherein the axes of rotation of the prisms extend essentially perpendicular to one another.

9. The device according to claim 3, wherein the light source comprises a laser or a laser diode.

10. The device according to claim 7, wherein the device forms part of an ophthalmologic Scheimpflug camera.

11. A device for projecting a light beam on an object, with a light source for generating the light beam, and with projection optics for transmitting the light beam from the light source to the object, wherein at least one prism with at least two essentially plane-parallel surfaces is arranged in a beam path of the light beam between the light source and the object as part of the projection optics, wherein the prism is movably supported and can be driven by a drive unit so that the light beam is shifted in a parallel fashion by an amount that depends on the position of the prism when the light beam passes through the plane-parallel surfaces of the prism, and wherein the light source emits an approximately line-shaped light beam.

12. The device according to claim 11, wherein the light beam is shifted by the prism in its longitudinal direction such that another line-shaped light beam is formed.

13. The device according to claim 11, wherein the device forms part of an ophthalmologic Scheimpflug camera.

14. A device for projecting a light beam on an object, with a light source for generating the light beam, and with projection optics for transmitting the light beam from the light source to the object, wherein at least one prism with at least two essentially plane-parallel surfaces is arranged in a beam path of the light beam between the light source and the object as part of the projection optics, wherein the prism is movably supported and can be driven by a drive unit so that the light beam is shifted in a parallel fashion by an amount that depends on the position of the prism when the light beam passes through the plane-parallel surfaces of the prism, and wherein the light source comprises several lamps that are adjacently arranged in a row.

15. The device according to claim 14, wherein the light beam is capable of being shifted by an amount that is greater than the distance between respectively adjacent lamps.

16. The device according to claim 14, wherein the several lamps comprise light-emitting diodes.

17. The device according to claim 14, wherein the device forms part of an ophthalmologic Scheimpflug camera.

18. A device for projecting a light beam on an object, with a light source for generating the light beam, and with projection optics for transmitting the light beam from the light source to the object, wherein at least one prism with at least two essentially plane-parallel surfaces is arranged in a beam path of the light beam between the light source and the object as part of the projection optics, wherein the prism is movably supported and can be driven by a drive unit so that the light beam is shifted in a parallel fashion by an amount that depends on the position of the prism when the light beam passes through the plane-parallel surfaces of the prism, wherein the device comprises a slit projector with a slit diaphragm, and wherein the prism shifts the light beam in the longitudinal direction of the slit.

19. The device according to claim 18, wherein the device forms part of an ophthalmologic Scheimpflug camera.

* * * * *